United States Patent [19]

Diamond et al.

[11] 4,389,348

[45] Jun. 21, 1983

[54] SELECTIVE HYDROGENATION OF DINITRILE TO OMEGA-AMINONITRILE AND SUPPORTED RHODIUM-CONTAINING CATALYST THEREFOR

[75] Inventors: Steven E. Diamond, New Providence; Frank Mares, Whippany, both of N.J.; Andrew Szalkiewicz, New York, N.Y.

[73] Assignee: Allied Corporation, Morris Township, Morris County, N.J.

[21] Appl. No.: 314,902

[22] Filed: Oct. 26, 1981

[51] Int. Cl.$^3$ ............................................ C07C 121/43
[52] U.S. Cl. ............................................. 260/465.5 R
[58] Field of Search .................... 564/490, 491, 492; 260/465.5 R

[56] References Cited

U.S. PATENT DOCUMENTS

| | | | |
|---|---|---|---|
| 2,208,598 | 2/1940 | Rigby | 260/465.5 R |
| 2,257,814 | 10/1941 | Rigby | 260/465.5 R |
| 2,762,835 | 9/1956 | Swerdloff | 260/465.5 R |
| 3,117,162 | 1/1964 | Rylander et al. | 564/490 |
| 4,311,859 | 1/1982 | Murtha et al. | 564/492 X |
| 4,313,018 | 1/1982 | Holy et al. | 564/490 X |

OTHER PUBLICATIONS

C. A., 47, 11230f, Badische, (1953).
C. A., 53, 11228h, Badische, (1959).
C. A., 52, 10158e, Badische, (1958).
Y. Takagi et al., Scientific Papers Institute Physical & Chemical Research (Japan), vol. 61, No. 3, pp. 114–117, (1967).
M. Freifelder et al., J. Am. Chem. Soc., vol. 82, pp. 2386–2389, (1960).
Chemical Abstracts, vol. 78, p. 462, 29279u, (1973).
Y. Takagi et al., Bulletin of the Chemical Society of Japan, vol. 28, No. 12, pp. 2119–2122, (1965).

*Primary Examiner*—Joseph Paul Brust
*Attorney, Agent, or Firm*—Alan M. Doernberg; Gerhard H. Fuchs

[57] ABSTRACT

A dinitrile is hydrogenated to an omega-aminonitrile with hydrogen in an aprotic solvent with a supported rhodium catalyst and ammonia present. The catalyst is prepared by hydrolyzing a rhodium (III) halide with strong aqueous base at elevated temperatures, drying the supported rhodium hydroxide at elevated temperatures and hydrogenating the dried product at elevated temperatures. High conversions, selectivity to aminonitrile and catalyst recyclability are achieved.

10 Claims, No Drawings

SELECTIVE HYDROGENATION OF DINITRILE TO OMEGA-AMINONITRILE AND SUPPORTED RHODIUM-CONTAINING CATALYST THEREFOR

BACKGROUND OF THE INVENTION

The present invention relates to the selective hydrogenation of nitriles such as adiponitrile to omega-aminonitriles such as eta-aminocapronitrile, employing a Group VIII metal-containing catalyst.

Group VIII noble metals are well known catalysts for various hydrogenations of organic compounds. The complete hydrogenation of adiponitrile to hexamethylenediamine is normally conducted with an iron, nickel and/or cobalt catalyst; however, platinum or palladium catalysts have also been suggested for this reaction. While the diamine product is widely used for producing diacid-diamine-type polyamides such Nylon-66, it would be desirable to also produce from the dinitrile the partial hydrogenation product, eta-aminocapronitrile, since this compound could be cyclized into caprolactam and polymerized to produce Nylon-6. While some attempts have been made with certain Group VIII metals or complexes to achieve selective hydrogenation, a process with high selectivity to eta-aminocapronitrile, or other omega-aminonitriles, at moderate conversion and with a catalyst which can be easily handled and conveniently recycled have not yet been found.

Rhodium has found few practical applications in hydrogenations. Rhodium metal itself, and inorganic rhodium oxides and salts supported on an inert support have been used in certain applications. Examples of processes employing such inert rhodium materials are contained in P. N. Rylander, *Catalytic Hydrogenation in Organic Synthesis* (New York 1979). Rhodium-based catalysts have not, however, been known to selectively hydrogenate dinitriles to aminonitriles.

Y. Takagi et al., *Scientific Papers institute Physical & Chemical Research (Japan)*, vol. 61, No. 3, pp. 114–17 (1967) discloses processes for hydrogenating nitriles with unsupported rhodium catalysts. In particular, rhodium hydroxide prepared by adding various amounts of sodium hydroxide to a hot aqueous solution of rhodium chloride was used as a catalyst for the hydrogenation of adiponitrile. Table II of the reference indicates that increased amounts of sodium hydroxide as a further additive increased the yield of hexamethylenediamine, but eventually retard the reaction rate. Lithium hydroxide was a superior additive. The yields were in most cases lower than the 80% yield reported using rhodium oxide prepared by the fusion of rhodium chloride with sodium nitrate.

M. Freifelder et al., *J. Am. Chem. Soc.*, vol. 82, pp. 2386–2389 (1960) employed 5% rhodium on alumina to hydrogenate aliphatic nitriles and especially 3-indoleacetonitrile. Ammonia was present to suppress production of secondary amines, but also reduced the catalytic activity of the rhodium. Ammonia is known to suppress secondary amine formation and reduce activity with other Group VIII metal catalysts.

U.S. Pat. Nos. 2,208,598 and 2,257,814, each to Rigby (Dupont 1940), and German Pat. Nos. 836,938 (1952), 848,654 (1952) and 954,416 (1956), all to BASF, disclose various catalytic processes directed to producing omega-aminonitriles from dinitriles employing miscellaneous catalysts including Raney nickel and iron, but not specifically any of the platinum group. See also U.S. Pat. No. 2,762,835 to Swerdloff (Celanese 1956).

Italian Pat. No. 845,999 to Montecatini Edison S.p.A. (1969) discloses the hydrogenation of dinitriles one or two carbons shorter than adiponitrile (e.g. succinonitrile) in the presence of a rhodium catalyst and ammonia to produce an omega-aminonitrile.

None of these patents provides a process with high selectivity to aminonitrile (compared to diamine and secondary amine) at high conversions of dinitrile with high rates of catalyst turnover and long catalyst life.

BRIEF DESCRIPTION OF THE INVENTION

It has been discovered that certain inorganic rhodium materials catalyze the hydrogenation of dinitriles to omega-aminonitriles. Accordingly the present invention includes a process for producing an omega amino nitrile which comprises reacting at a reaction temperature of between about 20° and about 200° C. a dinitrile of the formula $N\equiv C-(CH_2)_n-C\equiv N$ with n being an integer from 1 to 10 with hydrogen at a partial pressure of at least about one atmosphere in the presence of:

(a) ammonia in a molar amount at least equal to the molar amount of dinitrile present, (b) an aprotic solvent for the dinitrile, and (c) a rhodium-containing catalyst prepared by hydrolyzing a rhodium halide on a basic support selected from the group consisting of basic alumina, basic thoria, alkaline earth metal oxides and alkaline earth metal carbonates with strong aqueous base at a first temperature between about 50° C. and about 100° C. to produce a supported rhodium hydroxide, drying the supported rhodium hydroxide at subatmospheric pressure and a second temperature between about 50° C. and about 250° C., and hydrogenating the dried supported rhodium hydroxide at a third temperature between about 200° and about 400° C.; and recovering the omega-aminonitrile of the formula $N\equiv C-(CH_2)_n-NH_2$ as the major product.

DETAILED DESCRIPTION OF THE INVENTION

The dinitrile used as reactant in the present process may be adiponitrile (wherein n is 4 in the above formula) or may be other similar dinitriles of 3–12 carbons, such that n can vary from 1 to 10. Adiponitrile is most preferred, with somewhat less preferred dinitriles including malononitrile, succinnonitrile, glutaronitrile and pimelonitrile.

The dinitrile is present in the reaction mixture dissolved in an aprotic solvent such as tetrahydrofuran, dioxane, diglyme and similar ethers. The amount of solvent is not critical, but should be sufficient to dissolve the dinitrile and preferably to dissolve some hydrogen.

Hydrogen is normally present as a gas at low to moderate pressure in contact with the solution of dinitrile, with some hydrogen dissolved in the solvent. Partial pressures of hydrogen of at least about one atmosphere, and preferably between about 5 and 100 atmospheres are preferred. The hydrogen pressure correlates somewhat with the reaction temperature, which is suitably between about 20° C. and about 200° C., and is preferably between about 50° C. and about 150° C. The total operating pressure is generally equal to or only slightly above the pressure of hydrogen, with other gaseous materials present generally being limited.

Ammonia is present during the reaction to inhibit the formation of by-products, and especially cyclic amine (e.g. azacycloheptane and linear secondary amines (e.g. di(5-cyanopentyl)amine), both of which are formed by the condensation of an amine intermediate. Ammonia is present in molar amounts at least equal to the dinitrile, and preferably in a mole ratio of ammonia to dinitrile of about 5–15:1, more preferably about 10:1.

The rhodium-containing catalyst is one prepared by the hydrolysis, drying and reduction of a supported rhodium halide; with the conditions of all three preparative steps having a material affect on catalyst performance. The rhodium halide, e.g. $RhCl_3$, $RhBr_3$ or $RhI_3$, but preferably $RhCl_3$, is adsorbed on a basic support. Magnesium oxide (magnesia) is the preferred support, but other alkaline earth oxides (e.g. CaO, BaO, SrO) may be used, as may the corresponding alkaline earth carbonates. Basic thoria and alumina, that is the oxides of these metals rendered basic by treatment with strong bases such as alkali metal hydroxide, may be used. The water or hydroxyl content and surface area of the support is not critical, with magnesias of surface area from 1 to 250 $m^2/g$ surface area being suitable, for example. Treatments to reduce the hydroxyl content and increase the surface area, e.g. by calcining, are preferably performed on the support before adhering the rhodium halide.

The supported rhodium halide is hydrolyzed with strong aqueous base at a first elevated temperatures (e.g. 50°–100° C.). While the base is preferably an alkali metal hydroxide (e.g. NaOH, KOH or LiOH), it may also be a quaternary ammonium hydroxide or other strong soluble base. The stoichiometric amount of base (3:1) or a slight excess is preferably used, since less base will leave halide on the catalyst and a larger excess serves no useful purpose. The product of hydrolysis is a supported rhodium hydroxide.

The supported rhodium hydroxide is preferably washed before drying, suitable with water. A preferred procedure is for at least the final water rinse to be at elevated temperatures such as 50°–100° C.

The supported rhodium hydroxide is then dried, in one or more steps, with at least one stage being at subatmospheric pressure and a second elevated temperature (e.g. about 50°–250° C., preferably about 80–150° C., more preferably about 100° C.). The dried product, which may be part hydroxide and part oxide, or may be substantially all oxide, is then hydrogenated at elevated temperature prior to introduction of the dinitrile. Suitable third temperatures for hydrogenation of the dried product are about 200°–400° C., preferably about 250°–350° C. Hydrogen may be at atmospheric pressure at this stage or may be at a superatmospheric pressure.

The reaction temperature for hydrogenation of the dinitrile may be about 20° C. to about 200° C., and is preferably about 50°–150° C. The hydrogen partial pressure is at least one atmosphere, with increasing pressures causing greater reaction rates. Especially as the ammonia:dinitrile ratio increases above 1:1, the reaction rate with one atmosphere of hydrogen pressure may be insufficient, such that moderate pressures of 1.4–3.4 MPa (200–500 psig) or high pressures of 10.3 MPa (1500 psig) or higher are preferably used.

The reaction times are not critical, with contact times of minutes or hours being generally suitable. With a suitable catalyst, excessive times (determined by routine experiment, but frequently over four hours) will cause greater amounts of hydrogenation of the desired aminonitrile product to the undesired diamine by-product. A suitable range of reaction times are available whereat the dinitrile conversion is high, but the by-product diamine is still low.

EXAMPLE 1

203.1 mg of rhodium oxide pentahydrate ($Rh_2O_3.5H_2O$) were added to a stainless steel autoclave fitted with a glass liner and magnetic stir bar. Adiponitrile (10 mL), methanol (50 mL), tetrahydrofuran (20 mL) and ammonia (approximately 5 g) were then added to the autoclave which was then sealed. Hydrogen was introduced so that the total pressure was approximately 1500 psi (10.3 mPa). The autoclave was heated for approximately 4 hours at 75° C. At this time the autoclave was vented and opened. The liquid was filtered to remove the catalyst and analyzed by standard gas chromatographic techniques. The conversion of adiponitrile was 90% with a selectivity to epsilon-amino-capronitrile of 50%. The ratio of epsilon-amino capronitrile to 1,6-hexanediamine was approximately 3.2. A large amount of the cyclic secondary amine azacycloheptane and the linear secondary amine di(5-cyanopentyl)amine was also present.

EXAMPLE 2

Rhodium hydroxide was prepared in accordance with a known method as described in the *Bulletin of the Chemical Society of Japan* of 1965, volume 38, pages 2119–2122 at page 2121. 204.5 mg of this complex were added to a stainless steel autoclave equipped with a glass liner and magnetic stir bar. 3058.6 mg of adiponitrile and 20 mL tetrahydrofuran were then added after flushing with argon. Approximately 1.5 g of ammonia was then distilled in. The autoclave was sealed and pressurized to approximately 250 psi (1.7 MPa) with hydrogen gas. The autoclave was heated to 100° C. for a period of approximately 4 hours with constant stirring. At this time the autoclave was vented, opened and the catalyst was filtered. The filtrate was analyzed by standard gas chromatographic techniques to yield epsilon-aminocapronitrile as the major product. The conversion of adiponitrile was 53% with a selectivity to epsilon-aminocapronitrile of 89%. The ratio of epsilon-aminocapronitrile to 1,6-hexanediamine was approximately 16.

EXAMPLE 3

Example 2 was repeated with 202.0 mg of rhodium hydroxide and 3028.5 mg of adiponitrile in 20 mL tetrahydrofuran. No ammonia was added. After approximately 2 hours of heating at 75° C. the autoclave was vented and opened. Analysis of the reaction mixture revealed a conversion of adiponitrile of 67% with a selectivity to epsilon-aminocapronitrile of 81%. The ratio of epsilon-aminocapronitrile to 1,6-hexanediamine was approximately 4.4.

EXAMPLE 4

253.5 mg of rhodium on carbon catalyst (5%) were added to a stainless steel autoclave equipped with a glass liner and magnetic stir bar. 3163.5 mg of adiponitrile and 15 mL of tetrahydrofuran were then added. Approximately 5.4 g of ammonia were then distilled into the autoclave at which time it was sealed and pressurized to approximately 500 psi (3.4 MPa) with hydrogen gas. The autoclave was heated to 100° C. for a period of approximately 2 hours with constant stirring.

At this time the autoclave was vented, opened, and the catalyst was filtered. The filtrate was analyzed by standard gas chromatographic techniques to yield epsilon-aminocapronitrile as the major product. The conversion of adiponitrile was 78% with a selectivity to epsilon-aminocapronitrile of 55%. The ratio of epsilon-aminocapronitrile to 1,6-hexanediamine was approximately 8.8. A large amount of the cyclic secondary amine azacycloheptane was also present.

EXAMPLE 5

Example 4 was repeated with 254.2 mg of rhodium on alumina catalyst (5%) and 3174.3 mg adiponitrile. Analysis the the reaction mixture revealed a conversion of adiponitrile of 80% with a selectivity to epsilon-aminocapronitrile of 76%. The ratio of epsilon-aminocapronitrile to 1,6-hexanediamine was approximately 9.0.

EXAMPLE 6

The preparation of the supported rhodium on magnesia catalyst is illustrated below for the 2% by weight rhodium catalyst. Commercially available magnesia (Harshaw Chemical Company, ⅛" tablets) was ground and sieved. Only the 80–100 mesh fraction was utilized.

299.5 mg of rhodium trichloride trihydrate ($RhCl_3.3H_2O$) was dissolved in a minimum amount of water (approximately 2 mL). 5983.8 mg of the magnesia was formed into a thin paste by the addition of water. This paste was then added to the rhodium solution with constant stirring. This mixture was stirred overnight to allow the rhodium to adsorb onto the magnesia support. The originally white magnesia was now beige in color. The solid was dried in a vacuum oven at approximately 100° C. overnight.

3519.3 mg of this supported rhodium trichloride on magnesia were added to a round bottom flask. To this solid was added a slight excess of a 10% aqueous solution of sodium hydroxide. This suspension was heated to 90° C. for approximately 3 hours. At the end of this time the solid was filtered, washed with copious amounts of water (in some of these examples the water used was at 90° C., in others only room temperature water was used) until the pH of the filtrate was neutral and then placed in a vacuum oven at approximately 100° C. overnight. The resulting rhodium hydroxide on magnesia is yellow in color.

Prior to reaction the rhodium hydroxide or magnesia is reduced by hydrogen in a tube furnace at 300° C. for approximately 1 hour.

252.8 mg of this rhodium on magnesia catalyst (2%) were added to a stainless steel reactor equipped with a glass liner and magnetic stir bar. 3180.4 mg of adiponitrile and 15 mL of tetrahydrofuran were then added. Approximately 5.4 g of ammonia were then distilled into the autoclave at which time it was sealed and pressurized to approximately 500 psi (3.4 MPa) with hydrogen gas. The autoclave was heated to 100° C. overnight with constant stirring. At this time the autoclave was vented, opened, and the catalyst was filtered. The filtrate was analyzed by standard gas chromatographic techniques to yield epsilon aminocapronitrile as the major product. The conversion of adiponitrile was 74% with a selectivity to epsilon-aminocapronitrile of 93%. The ratio of epsilon-aminocapronitrile to 1,6-hexanediamine was approximately 18.

Examples 7–13 all employed a 5% by weight rhodium on magnesia catalyst prepared in an analogous manner to that described in Example 6. In all cases, except Example 7, the hydrogen pressure was approximately 500 psi (3.4 MPa). In Example 7, the hydrogen pressure was approximately 250 psi (1.7 MPa).

EXAMPLE 7

Example 6 was repeated with 255.3 mg of 5% by weight rhodium on magnesia catalyst, 3119.6 mg of adiponitrile, 20 mL of tetrahydrofuran and approximately 1.8 g of ammonia. After approximately 1 hour of heating at 100° C. the autoclave was vented, opened, and analyzed by standard gas chromatographic techniques. The conversion of adiponitrile was 81% with a selectivity to epsilon-aminocapronitrile of 79%. The ratio of epsilon-aminocapronitrile to 1,6-hexanediamine was approximately 7.0.

EXAMPLE 8

Example 6 was repeated with 252.5 mg of 5% by weight rhodium on magnesia catalyst, 3143.5 mg of adiponitrile, 15 mL of tetrahydrofuran, and approximately 5.2 gm of ammonia. After approximately 4 hours of heating at 100° C. the autoclave was vented, opened, and analyzed by standard gas chromatographic techniques. The conversion of adiponitrile was 82% with a selectivity to epsilon-aminocapronitrile of 89%. The ratio of epsilon-aminocapronitrile to 1,6-hexanediamine was approximately 13.

EXAMPLE 9

Example 6 was repeated with 254.8 mg of 5% by weight rhodium on magnesia catalyst, 3171.0 mg of adipnitrile, 15 mL of tetrahydrofuran and approximately 5.3 g of ammonia. After approximately 4 hours of heating at 100° C. the autoclave was vented, opened, and analyzed by standard gas chromatographic techniques. The conversion of adiponitrile was 86% with a selectivity to epsilon-amino capronitrile of 87%. The ratio of epsilon-aminocapronitrile to 1,6-hexanediamine was approximately 8.9.

EXAMPLE 10

Example 6 was repeated with 255.2 mg of 5% by weight rhodim on magnesia catalyst, 3166.7 mg of adiponitrile, 10 mL of tetrahydrofuran, and approximately 10 g of ammonia. After approximately 2 hours of heating at 100° C. no uptake of hydrogen gas was observed.

EXAMPLE 11

Example 6 was repeated with 218.9 mg catalyst 2657.8 mg of adiponitrile, 13 mL of methanol and approximately 4.4 g of ammonia. After approximately 30 minutes of heating at 100° C. the autoclave was vented, opened, and analyzed by standard gas chromatographic techniques. The conversion of adiponitrile was 88% with a selectivity to epsilon-aminocapronitrile of 71%. The ratio of epsilon-aminocapronitrile to 1,6-hexanediamine was approximately 6.7. A large amount of the cyclic secondary amine azacycloheptane was also present.

EXAMPLE 12

Example 6 was repeated with 252.5 mg of 5% by weight rhodium on magnesia catalyst, 3152.2 mg of adiponitrile, 15 mL of toluene and approximately 5.5 g of ammonia. After heating overnight at 100° C. the autoclave was vented, opened, and analyzed by standard gas chromatographic techniques. The conversion of adiponitrile was 91% with a selectivity to epsilon-aminocapronitrile of 69%. The ratio of epsilon-aminocapronitrile to 1,6-hexanediamine was approximately 8.6. A large amount of the cyclic secondary amine azacycloheptane was also present.

EXAMPLE 13

A high surface area magnesia (approximately 120 m$^2$/g) was prepared from the commercially available magnesia described in Example 6 (surface area approximately 12 m$^2$/g) by hydrolysis of the magnesia in water at 90° C. for approximately 2 hours followed by calcination in air at 400° C. for approximately 24 hours. A high surface area 5% by weight rhodium on magnesia catalyst was subsequently prepared as in Example 6 and was found to have a surface area of approximately 180 m$^2$/g.

Example 6 was repeated with 273.6 mg of the high surface area 5% by weight rhodium on magnesia catalyst, 2938.9 mg of adiponitrile, 15 mL of tetrahydrofuran and approximately 5.5 g of ammonia. After approximately 4 hours of heating at 100° C. the autoclave was vented, opened, and analyzed by standard gas chromatographic techniques. The conversion of adiponitrile was 87% with a selectivity to epsilon-aminocapronitrile of 85%. The ratio of epsilon-aminocapronitrile to 1,6-hexanediamine was approximately 8.8.

What is claimed is:

1. A process for producing an omega-aminonitrile which comprises reacting at a reaction temperature of between about 20° and about 200° C. a dinitrile of the formula $N{\equiv}C{-}(CH_2)_n{-}C{\equiv}N$ with n being an integer from 1 to 10 with hydrogen at a partial pressure of at least about one atmosphere in the presence of:

(a) ammonia in a molar amount at least equal to the molar amount of dinitrile present,
(b) an aprotic solvent for the dinitrile, and
(c) a rhodium-containing catalyst prepared by hydrolyzing a rhodium(III) halide on a basic support selected from the group consisting of basic thoria, alkaline earth metal oxides and alkaline earth metal carbonates with strong aqueous base at a first temperature between about 50° C. and about 100° C. to produce a supported rhodium hydroxide, drying the supported rhodium hydroxide at subatmospheric pressure and a second temperature between about 50° C. and about 250° C., and hydrogenating the dried rhodium hydroxide at a third temperature between about 200° and about 400° C.; and recovering the omega-aminonitrile of the formula $N{\equiv}C{-}(CH_2)_n{-}CH_2{-}NH_2$ as the major product.

2. The process of claim 1 wherein said aprotic solvent is tetrahydrofuran.

3. The process of claim 1 wherein ammonia is present at a molar ratio to dinitrile between about 5:1 and about 15:1.

4. The process of claim 1 wherein said reaction temperature is between about 50° and about 150° C.

5. The process of claim 1 wherein said second temperature is between about 80° and about 150° C.

6. The process of claim 1 wherein said third temperature is between about 250° and about 350° C.

7. The process of claim 1 or 2 or 3 wherein said basic support is magnesium oxide.

8. The process of claim 7 wherein n is 4.

9. The process of claim 1 or 2 or 3 wherein n is 4.

10. The process of claim 7 wherein the supported rhodium hydroxide is washed with water before drying.

* * * * *